US008992861B2

(12) United States Patent
Karkouche

(10) Patent No.: US 8,992,861 B2
(45) Date of Patent: Mar. 31, 2015

(54) BIOPARTICLE CAPTURE DEVICE, AND USE THEREOF

(76) Inventor: Bastien Karkouche, Antony (FR)

( * ) Notice: Subject to any disclaimer, the term of this patent is extended or adjusted under 35 U.S.C. 154(b) by 432 days.

(21) Appl. No.: 13/056,743

(22) PCT Filed: Jul. 24, 2009

(86) PCT No.: PCT/FR2009/051497
§ 371 (c)(1),
(2), (4) Date: Jan. 31, 2011

(87) PCT Pub. No.: WO2010/012941
PCT Pub. Date: Feb. 4, 2010

(65) Prior Publication Data
US 2011/0159533 A1 Jun. 30, 2011

(30) Foreign Application Priority Data
Jul. 29, 2008 (FR) .................................. 08 55210

(51) Int. Cl.
| | | |
|---|---|---|
| *B01D 21/00* | (2006.01) | |
| *B01D 35/00* | (2006.01) | |
| *B01D 41/00* | (2006.01) | |
| *G01N 1/18* | (2006.01) | |
| *G01N 1/40* | (2006.01) | |

(Continued)

(52) U.S. Cl.
CPC .............. *G01N 1/4077* (2013.01); *B01L 3/502* (2013.01); *C12M 47/02* (2013.01); *B01L 3/5082* (2013.01); *B01L 2300/0681* (2013.01); *B01L 2400/0478* (2013.01); *G01N 2001/4088* (2013.01)
USPC ............ 422/527; 422/534; 210/650; 436/177

(58) Field of Classification Search
CPC ....................................................... B01L 3/502
See application file for complete search history.

(56) References Cited

U.S. PATENT DOCUMENTS

| | | | |
|---|---|---|---|
| 4,553,553 A | | 11/1985 | Homann et al. |
| 4,945,921 A | * | 8/1990 | Okimoto ........................ 600/572 |

(Continued)

FOREIGN PATENT DOCUMENTS

| | | |
|---|---|---|
| DE | 3924862 A1 | 1/1991 |
| DE | 29919827 U1 * | 2/2000 |

(Continued)

OTHER PUBLICATIONS

International Search Report, dated Feb. 11, 2010, from corresponding PCT application.

(Continued)

*Primary Examiner* — Jill Warden
*Assistant Examiner* — Julie Tavares
(74) *Attorney, Agent, or Firm* — Young & Thompson

(57) ABSTRACT

A device for capturing suspended bioparticles in a liquid medium, includes:
- a tube (101) including first and second ends,
  - the first end of the tube being closed by the surface of a filter membrane (102) rendered stationary by adhesion onto the cross-section of the walls of the tube,
- a piston (104) including a rod (107) connected to a bearing element (108), the rod sliding along an axis parallel to the wall of the tube (101), and
- a block (103) of hydrophilic absorbent material placed inside the tube (101), inserted between (i) the inner surface of the filter membrane (102) and (ii) the piston (104) bearing element (108).

20 Claims, 9 Drawing Sheets

(51) Int. Cl.
*B01L 3/00* (2006.01)
*C12M 1/00* (2006.01)
*C02F 1/44* (2006.01)

(56) References Cited

U.S. PATENT DOCUMENTS

| | | | |
|---|---|---|---|
| 4,953,561 A * | 9/1990 | Guirguis | 600/584 |
| 5,139,031 A | 8/1992 | Guirguis | |
| 5,160,704 A | 11/1992 | Schluter | |
| 5,429,803 A | 7/1995 | Guirguis | |
| 5,484,572 A | 1/1996 | Katakura et al. | |
| 6,774,151 B2 * | 8/2004 | Malmgren et al. | 521/64 |
| 6,887,681 B2 * | 5/2005 | DiCesare et al. | 435/30 |
| 2005/0169809 A1 | 8/2005 | Centeleghe et al. | |
| 2007/0211563 A1 * | 9/2007 | De Vries | 366/139 |
| 2007/0284300 A1 | 12/2007 | Bidlingmeyer et al. | |

FOREIGN PATENT DOCUMENTS

| | | |
|---|---|---|
| DE | 29919827 U1 | 3/2000 |
| DE | 202007017400 U1 | 2/2008 |
| FR | 2869413 A1 | 10/2005 |
| JP | H02248836 A | 10/1990 |
| JP | H06500403 A | 1/1994 |
| JP | H06300752 A | 10/1994 |
| JP | H076746 U | 1/1995 |
| JP | H07103971 A | 4/1995 |
| JP | H0862210 A | 3/1996 |
| JP | H08508395 A | 9/1996 |
| JP | H11505714 A | 5/1999 |
| JP | H06501101 A | 8/1999 |
| JP | 2004245831 A | 9/2004 |
| JP | 2006006125 A | 1/2006 |
| WO | 02/48681 A2 | 6/2002 |
| WO | 03091704 A2 | 11/2003 |
| WO | 2008/076623 A2 | 6/2008 |

OTHER PUBLICATIONS

Translation of Japanese Office Action, dated Jun. 18, 2013, from corresponding JP application.

* cited by examiner

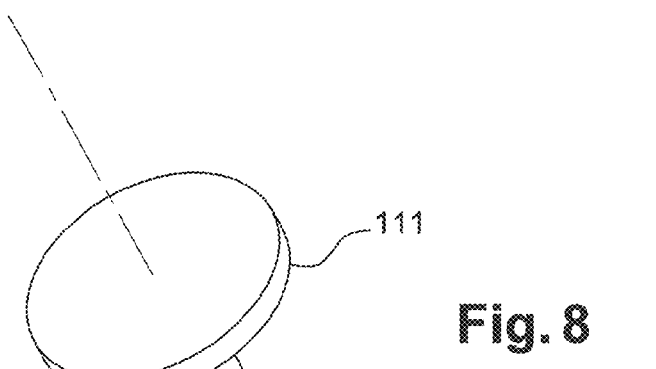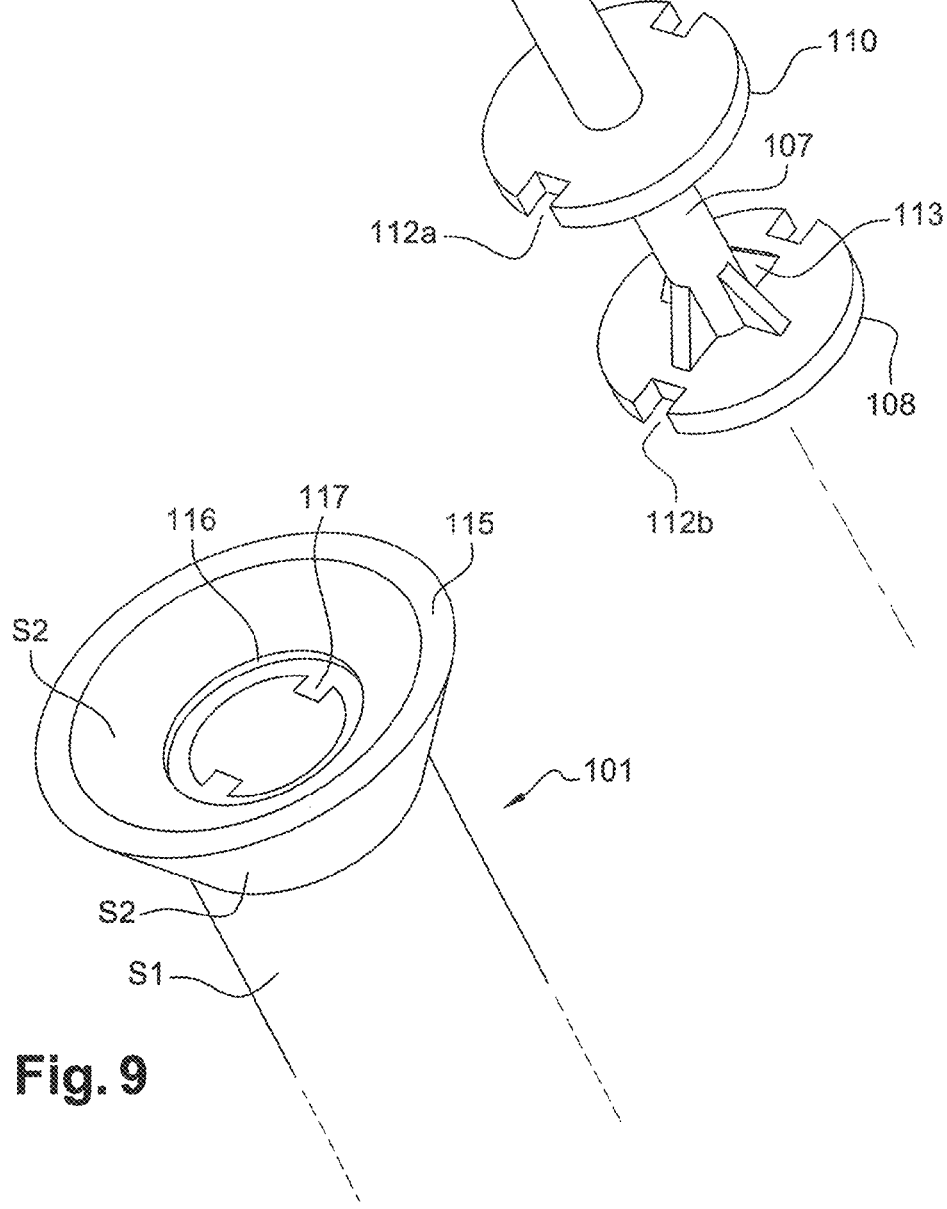

US 8,992,861 B2

BIOPARTICLE CAPTURE DEVICE, AND USE THEREOF

FIELD OF THE INVENTION

The present invention relates to the field of cell preparation analysis intended to be used for medical diagnosis.

STATE OF THE ART

Many methods exist in the medical diagnosis field, and more specifically cancer diagnosis, as well as many devices to be used for preparing biological samples intended to be subsequently submitted to a cytological analysis.

It can be observed a strong increase in the number of medical diagnosis procedures relying on cytological analyses together with the growing interest for preventive or early, periodical cytological diagnoses, which importance has been clearly demonstrated for the implementation of a patient early therapeutic caring to very significantly increase long term chances of survival or recovery chances.

Making cytological diagnoses at regular time intervals is all the more important since such techniques enable to detect diseases that are associated with vital prognosis, most of the time cancers, including breast cancer, excreto-urinary system tumors and uterine cancer.

In order to obtain quick results of the histological or cytological tests that have to be carried out on the numerous biological samples received each day by the anatomical pathologists, various integrated systems have been developed, making it possible to treat the biological samples in an automated way.

It is known automated image analysis systems enabling, from a cytological preparation fixed and stained on a micro slide, to help the technician identifying the most relevant cells or groups of cells for performing a medical diagnosis.

In addition, prior to the step of reading the cytological preparations, various automated systems for the treatment of biological samples have also been developed enabling to provide, from the initial biological sample, a cytological preparation, ready to analyze. To be mentioned are especially systems of this type marketed by the Cytyc company (Marlborough, Mass., United States).

Such automated systems adapted to the treatment of cell samples to analyze, suspended in a liquid medium, are described for example in the application PCT n° WO 2008/076623, or in the application PCT n° WO 03/091704. These systems comprise a filter through which all or part of the liquid medium is sucked-in, together with the cells that are first carried away and subsequently retained on the filter. Cells retained on the filter are then recovered and used for cytological tests, according to suitable methods.

In a system of the type of that described in the application PCT n° WO 2008/076623, the suction of the liquid medium containing the cells to be analyzed is performed by applying a negative pressure on the compartment downstream the filter, by means of a vacuum chamber. However, in order to subsequently carry out a reliable cytological analysis, a sufficient amount of cells should be retained on the filter to obtain a cell sample which would be representative of the previously collected cell population. Further, it should be avoided to retain on the filter an excessive number of cells, which would lead to the production of a cell sample wherein cells do form clusters and/or packings, that is to say a sample from which the subsequent cytological analysis could practically not be carried out. In particular, when cell clusters or packings are retained on the filter, the interesting cells might be substantially hidden in a cell layer which cannot be accessed through cytological analysis.

To remedy the drawbacks described hereabove, the device described in the application PCT n° WO 2008/076623 provides a system for regulating the strength of the generated vacuum so as to suck-in a suitable amount of cells onto the filter. In this regulation system, the amount of cells retained on the filter is indirectly evaluated in real time, by a means measuring the air flow rate between the filter and the vacuum source.

In practice, automated systems for making cell preparations intended to be used for cytological analysis work in a satisfactory manner. However, the various electronic regulation devices that are contained in these systems are very complicated, which significantly increases the dysfunction risk or even shut-down risk within the failing system. In addition, very sophisticated automated systems are very expensive, both upon buying and due to the need for secondary settings and scheduled maintenance effected by specialized technicians.

There is thus a need in the state of the art for alternative systems other than existing cytological analysis systems, which would enable to obtain cytological preparations which quality would be at least equivalent to that of known systems and which structure would be simpler.

SUMMARY OF THE INVENTION

Referring to FIGS. 1 and 4, it is an object of the present invention to provide a device for capturing suspended biological particles in a liquid medium, comprising:
- a tube (101) comprising first and second ends,
  - the first end of said tube being closed by the surface of a filter membrane (102) rendered stationary by adhesion onto the cross-section of the walls of said tube,
- a piston (104) comprising a rod (107) connected to a bearing means (108), said rod sliding along an axis parallel to the tube (101) wall, and
- a block (103) of hydrophilic absorbent material placed inside the tube (101), inserted between (i) the inner surface of the filter membrane (102) and (ii) the piston (104) bearing means (108).

The invention also relates to a method for capturing suspended biological particles in a liquid medium, wherein the hereabove described device is implemented.

The present invention also relates to a method for making a cytological preparation from a liquid medium containing suspended biological particles, wherein the hereabove described device is implemented.

DESCRIPTION OF THE FIGURES

FIG. 4 shows photon microscopy images of a cytological preparation transferred onto a glass slide, provided by a biological sample obtained from cervical cytology sample. The cytological preparation has then been fixed in a liquid medium of the PRESERVCYT® type, and thereafter submitted to a staining step according to the PARANICOLAOU method.

FIG. 8 is a diagram illustrating a particular embodiment of the rod (107).

FIG. 9 is a diagram illustrating a view of the upper part of one embodiment of the tube (101), which geometry has been specially adapted to receive the rod (107) according to the embodiment illustrated on FIG. 8.

DETAILED DESCRIPTION OF THE INVENTION

The applicant focused on developing a new device for capturing suspended biological particles in a liquid medium, essentially in order to prepare biological samples for cytological analysis.

In particular, the applicant sought to develop a new device of the hereabove type, which would be less expensive than the known devices and would simultaneously enable to obtain biological samples which quality would be at least equivalent to that of biological samples prepared with the known devices.

Upon researching, the applicant demonstrated that it was possible to obtain biological samples of a very high quality, in particular for a subsequent cytological analysis, with a filter membrane device wherein a liquid flow going through the filter is generated due to the absorption of said liquid by a hydrophilic absorbent agent placed immediately downstream the filter membrane, in the liquid flow direction. In particular, the applicant showed that with a hydrophilic absorbent agent of the type having a suitable absorbency, a liquid flow is produced which force or flow rate is sufficient for carrying away the bioparticles contained in a sample to be tested towards the filter membrane of the device in a stationary condition, therefore without requiring any displacement related to the stationary device immersed into the test sample, with respect to said sample.

Figure 4A:
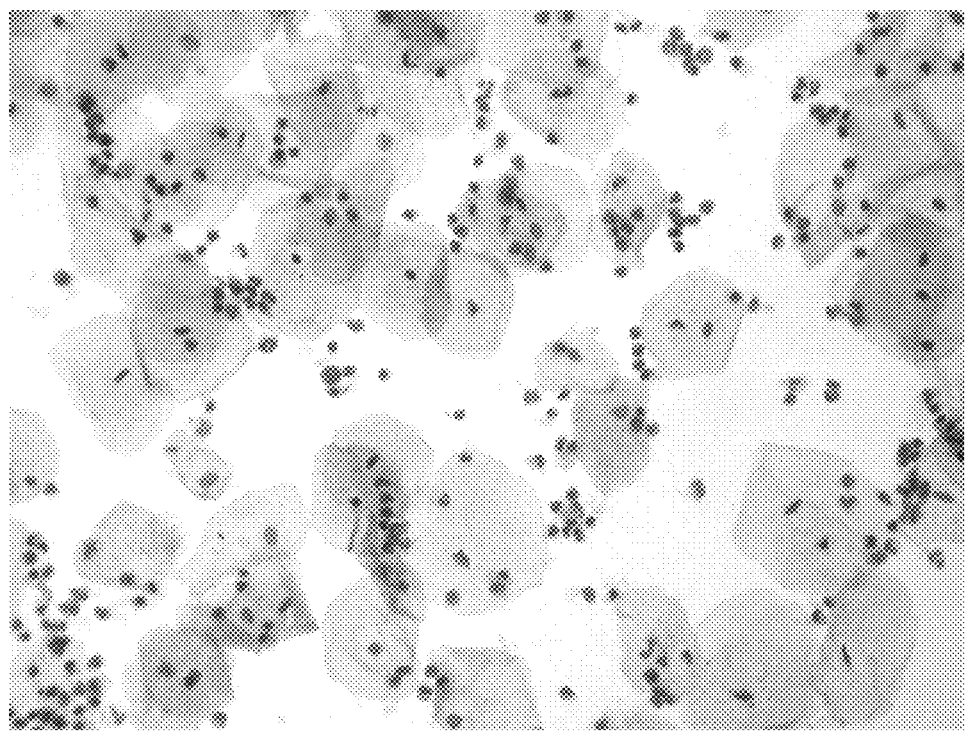
FIG. 4A illustrates a cytological preparation obtained with the device of the invention.
Figure 4B:
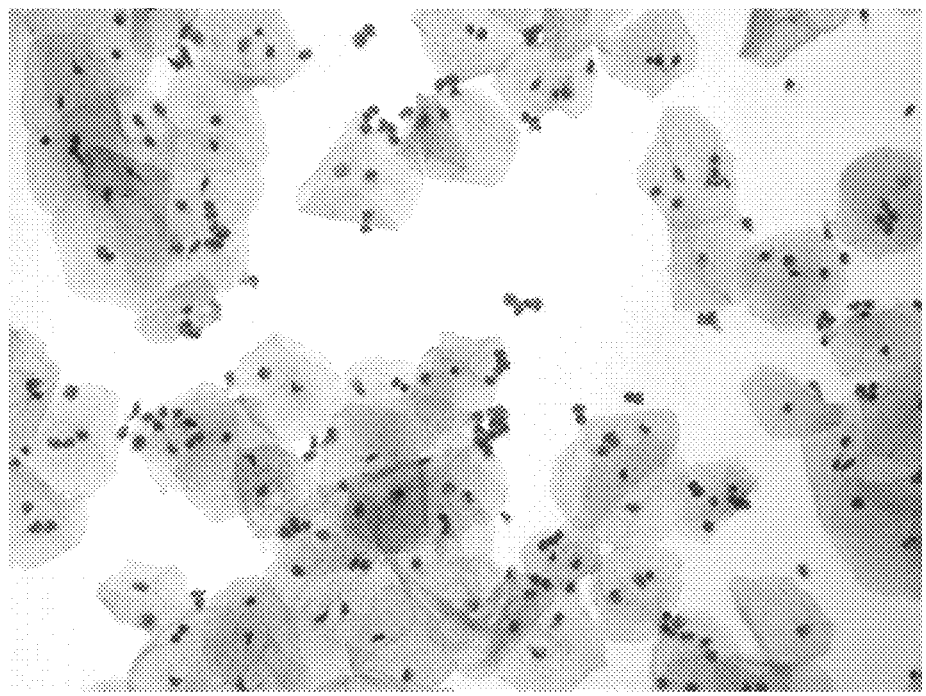
FIG. 4B illustrates a cytological preparation obtained with an automated system provided with a suction chamber under vacuum. Samples presented on FIGS. 4A and 4B are derived from the same cervical cytology sample.
Figure 5:
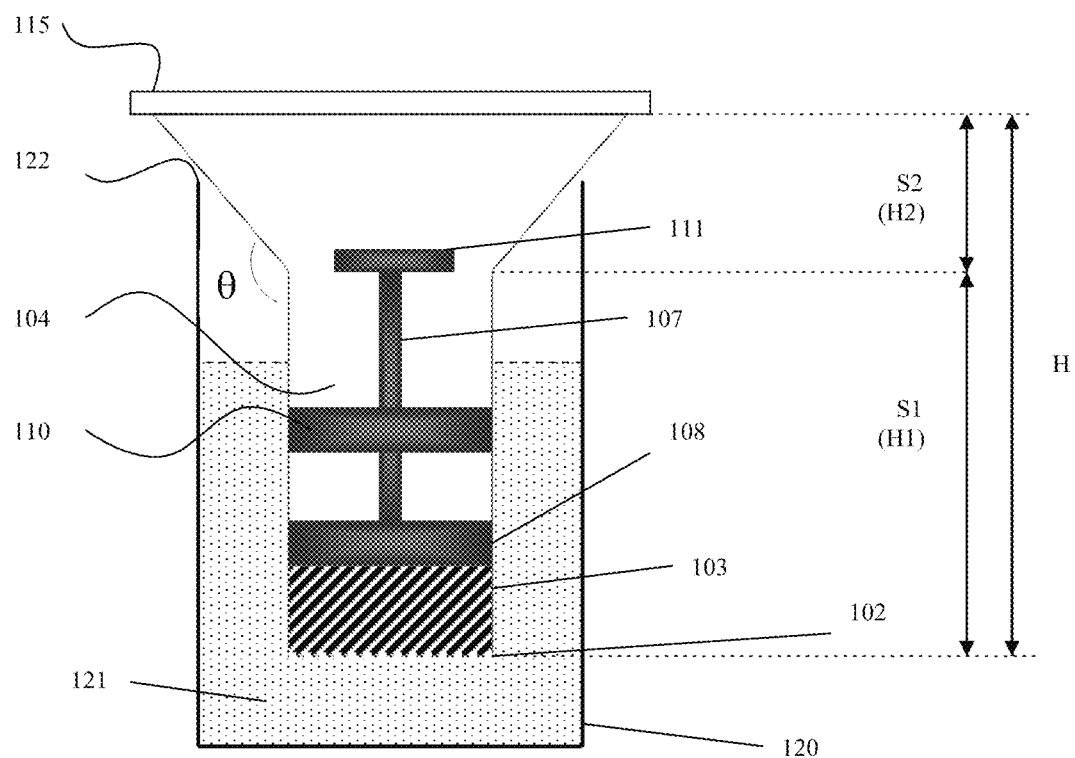
FIG. 5 is a diagram illustrating a vertical cross-section along the symmetry axis of one embodiment of the bioparticle capture device, immediately after having dipped said device in a container containing the biological fluid to be analyzed.
Figure 6:
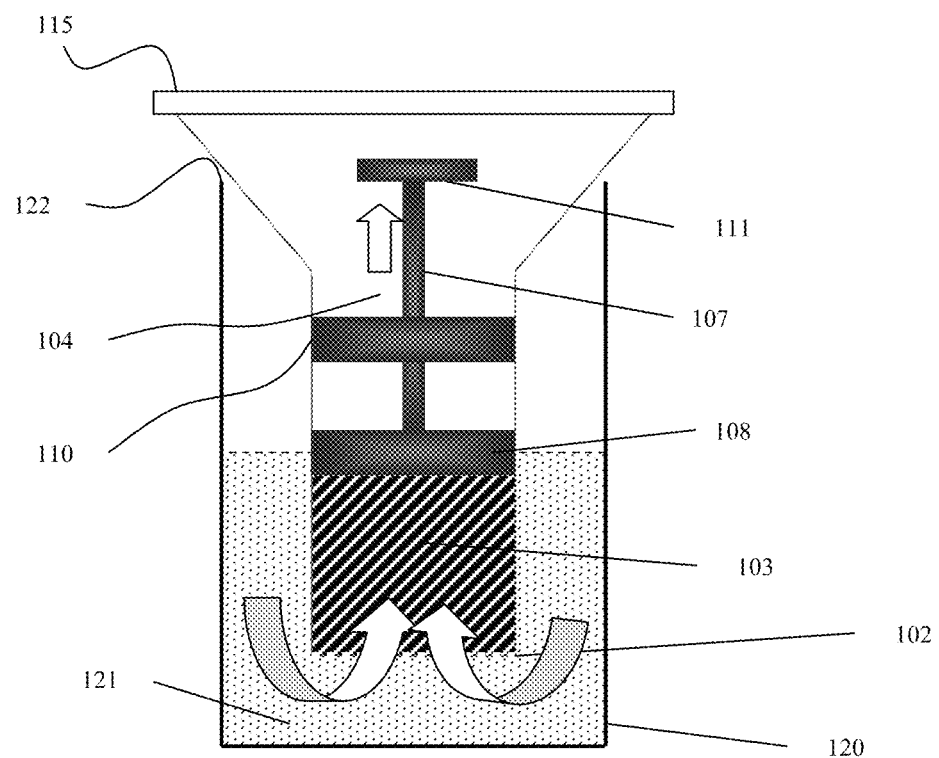
FIG. 6 is a diagram illustrating a vertical cross-section along the symmetry axis of one embodiment of the bioparticle capture device, when the device has been dipped, without being totally immersed, in a container containing the bioparticle suspension to be treated, for a time sufficient to retain the bioparticles on the surface of the filter membrane.
Figure 7:
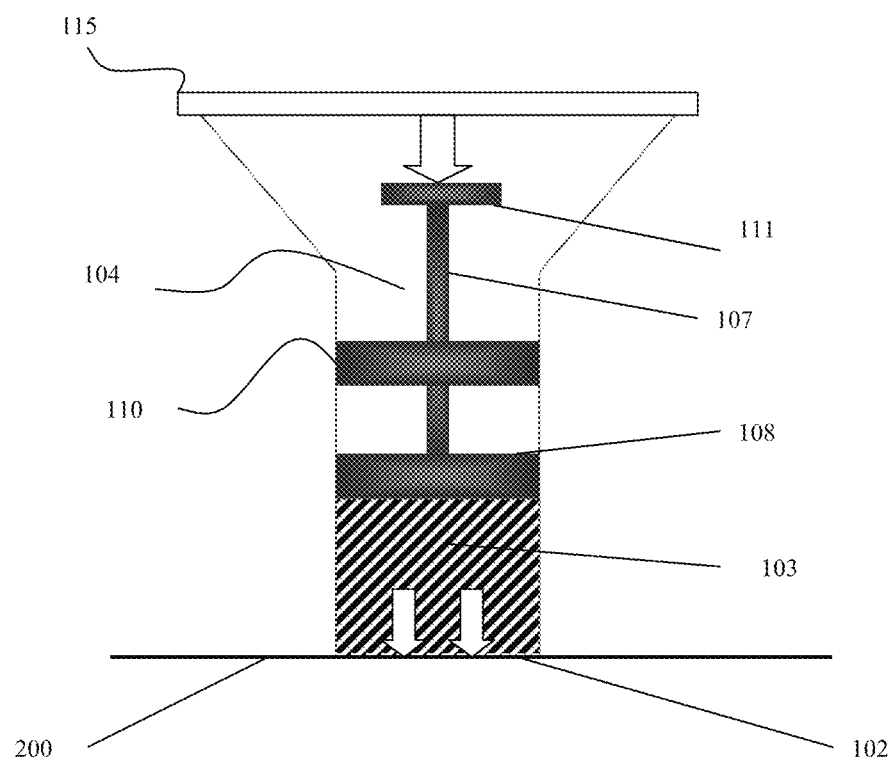
FIG. 7 is a diagram illustrating a vertical cross-section along the symmetry axis of one embodiment of the bioparticle capture device, after retention of the bioparticles on the filter membrane, when the piston rod is actuated for exerting a pressure on the absorbent block, so as to generate a liquid flow to the outside of the device aiming at removing the bioparticles from the filter membrane. In one particular embodiment illustrated on FIG. 7, the bioparticles previously adsorbed onto the surface of the filter membrane are transferred from the filter membrane onto the surface of a cytological analysis support, for example onto the surface of a microscope slide. On FIG. 7, the arrows represent the direction to which the piston is actuated.

Based on these surprising results, the applicant developed a new device a first embodiment of which is illustrated on FIGS. 1 to 4 and a second embodiment of which is illustrated on FIGS. 5 to 7. In addition, a specific embodiment of the device is more especially illustrated on FIGS. 8 and 9.

Figure 1:
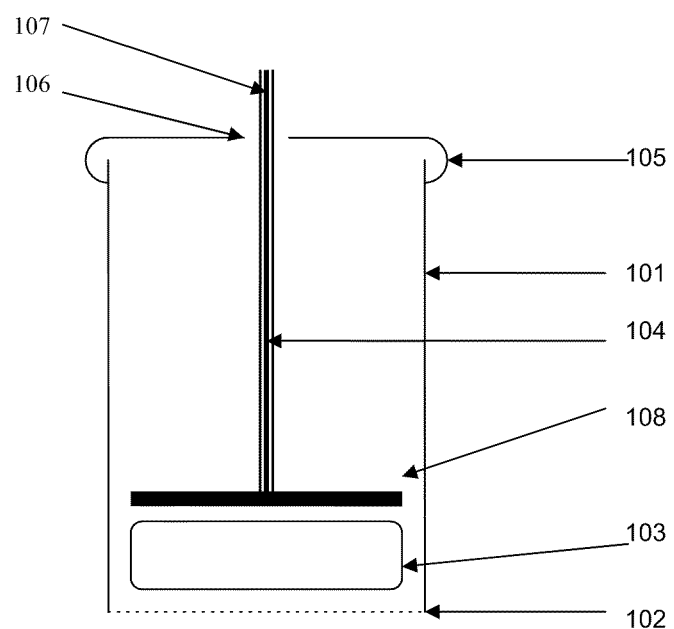
FIG. 1 is a diagram illustrating a vertical cross-section along the symmetry axis of one embodiment of the bioparticle capture device, before use.

The device of the invention for capturing suspended biological particles in a liquid medium is first of all described hereafter by referring to the drawings on FIGS. 1 and 5.

It is an object of the present invention to provide a device for capturing suspended biological particles in a liquid medium, comprising:
  a tube (101) comprising first and second ends,
    the first end of said tube being closed by the surface of a filter membrane (102) rendered stationary by adhesion onto the cross-section of the walls of said tube,
  a piston (104) comprising a rod (107) connected to a bearing means (108), said rod sliding along an axis parallel to the tube (101) wall, and
  a block (103) of hydrophilic absorbent material placed inside the tube (101), inserted between (i) the inner surface of the filter membrane (102) and (ii) the piston (104) bearing means (108).

As used herein, a "biological particle" is intended to mean any solid particle insoluble in an aqueous liquid medium which might be present in a biological material collected on the body of an animal or a plant multicellular living organism, advantageously an animal multicellular living organism, preferably a mammal, including humans. The bioparticles encompass tissue micro-fragments, possible microorganisms, living cells, dead cells, anucleated cell bodies such as erythrocytes and platelets (thrombocytes), fragments, cell debris, as well as possible crystals and light solid foreign bodies. The biological particles thus encompass any substance insoluble in an aqueous liquid medium, including insoluble protein substances, such as pectin or protein substances derived from fibronectin, for example protein substances derived from fetal fibronectin which represent a clinical parameter indicating a risk for preterm delivery.

The device of the invention is described hereafter in more detail, in particular through the description of a plurality of specific structural characteristics and, if applicable, of technical effects resulting from those structural characteristics. Various embodiments of the device of the invention are described hereafter, referring especially to the illustration of the miscellaneous structural characteristics shown on the figures. It should be noted that a particular embodiment of the device of the invention may comprise only one of the numerous specific technical characteristics that will be detailed hereunder, or many combined specific characteristics. However, just for the sake of concision and clarity in the statement, the figures illustrate embodiments of the device of the invention wherein several of the specific technical characteristics detailed hereafter are combined, each of which may be present individually or in combination with one or more other specific characteristics, in the device of the invention.

As will be described in detail further in the description, capturing biological particles by means of the device of the invention is performed (i) by dipping at least the filter membrane containing-end of the device into the liquid medium containing suspended bioparticles, without the upper end of the device being itself immersed, and (ii) by maintaining the device in said liquid, preferably in a fully stationary position within said liquid, for a time sufficient for capturing the particles on the filter membrane thanks to a liquid flow resulting from the absorption of said liquid by the block of absorbent agent. It should be noted that the absorbent agent consists in a hydrophilic absorbent agent which progressively swells as increases the volume of absorbed liquid, as is shown for example on each of FIGS. 2 and 6. Generally, the applicant observed that the swelling of the absorbent agent goes on, even after the device has been withdrawn from the liquid containing the suspended bioparticles therein. The applicant believes that after the device has been withdrawn from the liquid containing the particles suspended therein, the persistence of the absorbent agent swelling enables the reduced volume of liquid to be absorbed upon contacting the filter membrane, in particular upon contacting the outer surface of the filter membrane, said reduced volume of liquid being taken away together with the device, in particular due to surface tension force as well as to the force of the liquid flow generated by the block of absorbent material. The applicant believes that the swelling of the block of absorbent material which can be observed after withdrawal of the device of the invention from the liquid medium comprising the bioparticles is able to generate a residual suction pull towards the tube inside (101), which goes through the filter membrane (102), and which helps retaining efficiently the bioparticles on the outer surface of said filter membrane (102), without simultaneously altering the physical integrity of said biological particles.

Thus, in preferred embodiments, the block (103) of absorbent agent is made of a hydrophilic material that swells when contacting a liquid medium, in particular an aqueous liquid medium.

Preferably, the block of absorbent agent has an absorption capacity of aqueous liquid media of at least twice its own dry weight and more preferably up to at least three or four times its own dry weight.

Preferably, the block of absorbent agent can swell to a two-fold increase in volume through absorption of a liquid medium, and more preferably to an at least three- or four-fold increase in volume, as compared to its initial dry volume.

Generally speaking, the dimensions of the block (103) of absorbent material are adapted for enabling an easy insertion of the block (103) into the tube (101).

In some embodiments of the device, the dimensions of the block (103) are adapted so that the block (103) can be easily displaced along the tube (101). In these embodiments, the block (103) of absorbent material is inserted at the end of the tube (101) intended to receive the plug (105) and gets positioned upon contacting the filter membrane (102) simply due to gravity. In these embodiments of the device, the swelling properties of the block (103) of absorbent material are such that the outer wall of the block (103) does not quickly come in contact with the inner wall of the tube (101), but rather swells in the direction of its vertical axis by pushing the piston back towards the upper part of the tube (101), generally after 15 to 20 seconds following the immersion of the lower end of the device provided with the filter membrane (102).

In other embodiments of the device, the dimensions of the block (103) are such that they require forced insertion and displacement of the block (103) in the tube (101) until the block (103) be positioned at the other end of the tube (101) in contact with the filter membrane (102). The time required once the lower end of the device has been dipped may vary.

For manufacturing a block (103) of absorbent material, the person skilled in the art may use any type of hydrophilic absorbent agent having the swelling properties described hereabove, which is commonly commercially available.

Illustratively, the one skilled in the art may use an absorbent agent made of viscose, preferably of a compressed viscose material. In some particular embodiments, one may use a viscose material in the form of a textile "non woven" lap of viscose, folded on itself again and again, so as to form a suitably sized laminated block of viscose. Most preferably, said laminated viscose block is submitted to a compression step so as to obtain a compressed, laminated viscose block with outstanding absorbance properties due to (i) the viscose's high capacity to absorb aqueous liquid media and (ii) the liquid suction force resulting from the high increase in volume of the compressed viscose when contacting an aqueous liquid medium.

According to another illustration, for obtaining a block (103) of absorbent agent, one may use a super-absorbent agent, well known from the one skilled in the art.

The person skilled in the art may use a super-absorbent agent of the hydrogel type. For example, the person skilled in the art may use as a hydrophilic absorbent agent a polymer of the crosslinked sodium polyacrylate polymer type, which may be obtained through a polymerization reaction of acrylic acid combined with sodium hydroxide in the presence of a polymerization initiator. Crosslinked sodium polyacrylate-based super-absorbent agents are known per se and are broadly commercially available.

As an absorbent agent of the super-absorbent type, it may also be used a copolymer of polyacrylamide, a copolymer of maleic anhydride and ethylene, crosslinked carboxymethyl cellulose, copolymers of polyvinyl alcohol, or crosslinked polyethylene oxide.

The swelling capacity of the hereabove mentioned super-absorbent agents is variable but corresponds to at least 10 or at least 20 times the dry volume thereof. As an example, the swelling capacity of a super-absorbent agent of the crosslinked sodium polyacrylate type may reach 30 to 60 times the dry volume thereof.

Generally speaking, the tube (101), the plug (105), the piston (104) and the filter membrane (102) are of a conventional type.

For example, the tube (101) fitted with the filter membrane (102) may be of the type of those which are commonly used as filters for use in biological sample treatment automated systems for cytological analysis. Generally, the filter membrane simply adheres to or is welded to the thickness of the wall of one of the ends of the tube (101).

Illustratively, the tube (101), as well as the rod (107) and the piston (104) bearing means (108) may be made of any type of plastics, including polyvinyl chloride (PVC), polystyrene or polyethylene.

Preferably, whatever the embodiment considered, the tube (101) comes as a monoblock, which may be made for example through a molding process.

As a further illustration, the piston (104) bearing means (108) may be made of another material, for example elastomer, latex or silicone.

Advantageously, the filter membrane consists in a filter for cell filtration of a known type in the field of cytology, for example a polyester filter or a polycarbonate filter. Illustratively, one may use suitable filter membranes marketed by the Millipore company (Billerica, Mass., United States). To be mentioned are also suitable filter membranes marketed by the Whatman-GE Healthcare company (Versailles, France).

Generally speaking, in a bioparticle capture device of the invention, a filter membrane may be used, having a given pore size, selected in the range from 1 µm to 25 µm.

In some embodiments of the bioparticle capture device of the invention, a filter membrane is used having a given pore size selected in the range from 1.5 µm to 2.5 µm, preferably of 2 µm. The filter membrane reference n° 7060-2511 marketed by the Whatman-GE Healthcare company may be used for example. With a filter membrane of this type, the device of the invention can capture all the interesting bioparticles for a subsequent cytological analysis, whatever the tissue nature or origin of the initial biological sample that was collected.

In some other embodiments of the bioparticle capture device of the invention, a filter membrane is used, having a given pore size selected in the range from 3 µm to 10 µm, preferably of 5 µm or 7 µm or 8 µm. The filter membrane reference n° TMTP-02500 marketed by the Millipore company may be used for example. The filter membrane reference n° TTT-P02500 marketed by the Millipore company may also be used. Filter membranes Cyclopore® PC marketed by the Whatman-GE Healthcare company may also be used, such as 5 µm membranes (Ref. 7060-2513; 7060-4713), 8 µm membranes (Ref. 7060-2514; 7060-4714) or 10 µm membranes (Ref. 7060-2515; 7060-4715). With a filter membrane of this type, the device of the invention can only retain cells with a large size, for example of the type of epithelial cells contained in an initial biological sample from a vaginal sample or a cervico-vaginal smear.

As shown on FIGS. 4A and 4B, the applicant demonstrated that the device of the invention enables the capture of bioparticles which are carried away towards the filter membrane (102) exclusively by the liquid flow generated by the suction pull force resulting from the swelling of the block (103) of absorbent material contained in the device in a stationary condition, in order to subsequently carry out the cytological preparations which quality is at least as good as that of the cytological preparations obtained with the known devices. With the device of the invention, it may be performed a large diversity of cytological preparations according to methods that are known per se, for example by transferring the bioparticles adsorbed onto the surface of the filter membrane into an analysis medium or onto a suitable analysis support. The bioparticles adsorbed onto the surface of the filter membrane may be for example transferred to an analysis liquid medium, for example of the type comprising a substance for fixing biological particles, including a cell fixation agent. According to another conventional alternative, said bioparticles may be transferred onto the surface of a biological analysis support, for example onto the surface of a glass slide.

The applicant has shown that the cytological preparations obtained with the device of the invention enable to preserve the physical or biological integrity of the bioparticles contained in the test sample. The preservation of the physical or biological integrity of the bioparticles present in the final cytological preparation is also due to the fact that the bioparticles adsorbed onto the surface of the filter membrane (102) are then simply transferred to the surface of the cytological analysis support, generally a glass plate, by contacting the surface of the filter membrane with the surface of the cytological analysis support and by transferring the bioparticles of the first to the second surface by just exerting a short pressure onto the piston, for example for 0.5 to 5 seconds.

The transfer of the bioparticles from the filter membrane of the device to the analysis medium, for example to the surface of the cytological analysis support, may thus be effected by a simple contact, without requiring any pressure of the filter membrane (102) to the surface of the cytological analysis support. Indeed, pressing the filter membrane (102) onto the cytological analysis support, so as to transfer the biological particles from said filter membrane to the surface of said support, would cause at least part of the bioparticles to collapse, where such physical damaging of the bioparticles might produce poor quality final cytological preparations and, at worst might substantially alter diagnosis results.

As previously described, the piston (104) of the device of the invention slides inside the tube (101) along an axis which is parallel to the axis of the cylinder wall of said tube (101). In some embodiments, the device of the invention does not comprise any special means to force the sliding of the piston (104) along the expected axis, because the sliding axis of the piston (104) is determined as being perpendicular to the upper surface of the block (103) of absorbent material. In other embodiments, the device of the invention comprises at least one special means to force the sliding of the piston (104) along the expected axis, as for examples in the embodiments of the device illustrated respectively on FIGS. 1 and 5.

In the embodiment illustrated in FIG. 1, the second end of the tube (101) is closed by a plug (105) comprising a central hole (106). In this particular embodiment of the device, the rod (107) of the piston (104) slides, through the central hole (106), from either side of the plug wall (105). The central hole (106) acts as a sliding guide for the rod (107) so as to ensure a vertical sliding of the latter, along an axis parallel to the wall of tube (101).

In the embodiment of the device of the invention illustrated on FIGS. 5 and 8, the rod (107) of the piston (104) slides vertically, along an axis which is parallel to the axis of the walls of the tube (101) thanks to the presence of a disk (110) fixed on the rod (107). This particular embodiment of the device will be described in more detail further in the present description.

The geometry of the device of the invention, and in particular the geometry of the horizontal cross-section of the tube (101), may be very varied.

Thus, in some preferred embodiments of the device of the invention, as illustrated on FIG. 1, the tube (101) has a horizontal circular cross-section and as such the tube (101) is cylindrical. In this particular embodiment, the block (103) of absorbent material also has preferably a cylindrical form. Most preferably, the diameter of the block (103) of absorbent material is slightly lower than the tube (101) inner wall diameter, so that the outer wall of the block (103) of absorbent material be not in contact with the inner wall of the tube (101), once the lower end of the device is immersed in the container containing the bioparticle suspension.

Generally speaking, the block (103) of absorbent material is fixed at the end of the tube (101) fitted with the filter membrane (102) without requiring any special fixing means. In those embodiments where the dimensions of the block (103) of absorbent material are smallest that those of the inner surface of the tube (101) wall, the block (103) is fixed by simple gravity. The positioning of the block (103) is further improved through the piston (104) weight, the bearing means (108) of which may be initially positioned to contact the upper surface of the block (103). The positioning of the block (103) may also be ensured through a gentle, direct manual or mechanical pressure on the rod (107). In these embodiments where the dimensions of the block (103) are the same or higher than those of the inner surface of the tube (101) wall, the block (103) is fixed due to the combined gravitational force and to the bearing force of the block (103) wall onto the inner surface of the tube (101) wall.

In other embodiments of the device of the invention, the horizontal cross-section of the tube (101) may be oval, square, rectangular or other. It goes without saying that for simply practicity's sake as regards ease of construction and use, the preferred embodiment of the device of the invention is that with the circular tube (101) cross-section, the tube (101) being therefore of cylindrical form. As will be discussed later in the description, a tube (101) having a cylindrical form includes embodiments wherein the tube (101) is strictly cylindrical just on part of height thereof, where said tube (101) may have a composite form and further comprise, in addition to a cylindrical section, also at least one tapered section. It should be noted that a tube (101) having, like the one illustrated on FIG. 5, a cylindrical section topped by a tapered section has, on all the height thereof, and whatever the section considered, a horizontal circular cross-section.

According to another aspect of the device of the invention, the dimensions of the piston (104) bearing means (108) are chosen so that the piston (104) moves freely along the vertical axis of the tube (101). Thus, in these preferred embodiments of the device, the edges of the piston (104) bearing means (108) are not continuously contacting the surface of the inner wall of the tube (101). This particular characteristic of the device of the invention means that a gas or a liquid flow can freely flow between (i) the lower compartment of the tube (101) delimited by the filter membrane (102) and the lower surface of the piston (104) bearing means (108), (ii) the upper compartment of the tube (101) delimited by the upper surface of the piston (104) bearing means (108) and the upper end of the tube (101) located at the plug (105) and (iii) the outer atmosphere with which the inner volume communicates through the central hole (106) of the plug (105).

Illustratively, when the tube (101) consists in a cylindrical tube, the piston (104) bearing means (108) is advantageously circular and its diameter is slightly lower than the inner wall diameter of the tube (101), so as to ensure an easy displacement of the piston along the vertical axis of the tube (101). For example, the present invention includes the embodiment wherein the tube (101) inner wall diameter is 21 mm and the piston (104) bearing means (108) diameter is 20 mm.

Another particular embodiment of the device of the invention for capturing suspended bioparticles in a liquid medium is illustrated, during the different steps of a method for implementing the same, on FIGS. 5 to 7.

By referring more particularly to FIG. 5, this particular embodiment of the device of the invention comprises an upper part expanded as a funnel, which promotes the stability thereof within the liquid in which said device is dipped when used for an analysis, for example a cytological analysis of a biological tissue sample.

In the embodiment illustrated on FIG. 5, the tube (101) comprises two sections forming a continuous outer surface, respectively:
 a first section S1 of the cylindrical type, one end of which consists in the first end of said tube which is closed by the surface of a filter membrane (102), and which other end forms a continuous outer surface with a third section, and
 a third section S2 of the tapered type, which end with the smallest diameter forms a continuous outer surface with said first cylindrical section, and which end with the largest diameter consists in the second end of the tube (101).

On FIG. 5, the device of the invention was placed in a container (120) filled with a liquid (121) to be analyzed. As can be seen on FIG. 5, the outer surface of the tapered section (S2) of the tube (101) comes to rest, because of the gravitational force, leaning on the container (120) edges (122), so as to block the vertical movement of the tube (101) at a given position within the container (120).

It is thus necessary for the external diameter D1 of the second end, that is to say the upper end, of the tube (101) to be higher than the inner diameter D2 of the container containing the liquid to be analyzed.

Generally, the containers adapted for analyzing biological samples, in particular containers adapted to cytological analyses, possess determined standard dimensions. As a consequence, the dimensions of the device of the invention, and in particular those of the tapered section S2 as well as those of the tube (101) total height may be determined beforehand to be adapted to each conventionally used biological analysis container.

As is shown on FIG. 5, suitably combining (i) the height H1 of the section S1 of the tube (101), (ii) the angle θ formed between sections S1 and S2 outer walls and (iii) the height H2 of the section S2, makes it possible for the surface of the filter membrane (102) located at the first end of the tube (101) to be suitably spaced apart from the bottom of the analysis container (120), so that the outer surface of the filter membrane (102):
 be neither supported by, nor contacting in any manner, the bottom surface of the analysis container (120), and
 be positioned at a small distance from the bottom surface of the analysis container (120) so as to optimally enable the recovery of the suspended bioparticles and to thus reduce for some particles the risk of incomplete recovery, for example for high density particles, that may be suspended in the lower part of the container (120).

In some embodiments, the height H1 of the section S1 represents at least two thirds of the total height H of the tube (101).

In the embodiment of the tube (101) illustrated on FIG. 5, said tube comprises in addition an annular shoulder at its upper end.

In this particular embodiment of the tube (101), the end with the largest diameter of the section S2 of the tube (101) comprises a flat, annular shoulder (111) which plane lies perpendicularly to the edges of the section S1 of said tube (101). The shoulder (11) forms a flat section, that is to say an annular surface which plane lies perpendicularly to the vertical axis of the tube (101) and which inner diameter coincides with the largest diameter of the tapered section S2. Preferably, the end of the section S2 and the shoulder (115) form a continuous outer surface.

Preferably, in this embodiment of the tube (101), the dimensions of the tube (101) are chosen so that (i) the external diameter of the end with the largest diameter of the section S2 be lower than the inner diameter of the vertical walls of the container (120) and so that (ii) the external diameter of the annular shoulder (115) be higher than the inner diameter of the vertical walls of the container (120). Depending on the arrangement, when the tube (101) is engaged in the analysis container (120), the surface of the shoulder (115) is in contact with the upper edges of the container (120) (not shown on FIG. 5). In this embodiment, the distance between the outer surface of the membrane (102) of the tube (101) and the surface of the bottom of the container (120) is determined by the difference between (i) the height H which is the sum of heights H1 and H2 respectively of sections S1 and S2, and (ii) the height between (ii-1) the junction of the container (120)

vertical wall with the inner surface of the bottom of said container and (ii-2) the upper edges of the container (120) walls.

In the embodiment of the device of the invention illustrated on FIG. 5, the rod (107) of the piston (104) is fitted with a disk (110) which is placed in an intermediate position between the bearing means (108) and the upper end of the rod (107). One embodiment of this type of piston (104) is shown in detail on FIG. 8.

Thus, in some embodiments of the bioparticle capture device of the invention, said device is characterized in that a disk (110) is fixed on the rod (107), the diameter of said disk (110) being determined so that it enables the guiding of the rod (107) along an axis parallel to the walls of the tube (101). In these embodiments of the device, the disk (110) enables the piston (104) to slide along an axis which is maintained vertical for all the stroke of said piston.

Referring to FIGS. 5 and 8, some embodiments of the device of the invention have the rod (107) of the piston (104) fitted with a disk (110). In the embodiment of the piston (104) illustrated on FIG. 8, said piston comprises a plunger means (111) intended to transmit a vertical supporting force, from the top to the bottom of the piston, so as to transfer the bioparticles adsorbed onto the filter membrane to the medium or to the cytological analysis support, or even to release part of the liquid that may be contained in the tube (101), in particular in the block of absorbent material.

In one particular embodiment of the piston (104) illustrated on FIG. 8, the vertical supporting force which is exerted through the plunger means (111) is transmitted in a substantially uniform manner to the whole surface of the pusher means (108), thanks to one or more reinforcements (113). Each reinforcement (113) (i) forms an integral part, on one of sides thereof, of the rod (107) wall, and (ii) forms an integral part, on a third side, of the upper surface of the pusher means (108). Preferably, a reinforcement (113) is triangular with one of the three sides thereof fixed to the outer wall of the rod (107) and another of the three sides thereof fixed to the upper surface of the pusher means (108). In this preferred embodiment, a reinforcement (113) comes as a square. Most preferably, the length of the reinforcement (113) side which forms an integral part of the pusher means (108) represents at least half the distance, more preferably at least two thirds thereof, separating (i) the outer edge of the pusher means (108) from (ii) the wall of the end of the rod (107) which is fixed to the pusher means (108).

The piston (104), when fitted with reinforcements (113), comprises preferably at least two, and more preferably at least four, reinforcements (113). Generally, the number of reinforcements (113) may be 2, 3, 4, 5 or 6 reinforcements.

The presence of the reinforcements (113) ensures the transmission of an upper pressure substantially uniformly to the whole surface of the block (103) of hydrophilic absorbent material when using the device, and enables therefore to release the liquid contained in the device, through the filter membrane (102), with a pressure substantially uniformly distributed on the whole surface of the filter membrane (102). Thus, when implementing this device special embodiment of the invention, the detachment of the bioparticles that may have been previously adsorbed on the surface of the filter membrane (102), to be transferred to the medium or to the cytological analysis support, is also effected in a substantially uniformly manner, from the whole outer surface of said filter membrane (102), generally to the surface of the cytological analysis support.

In the embodiment of the piston (104) illustrated on FIG. 8, the disk (110) comprises two recesses or slots (112). This embodiment of the piston (104) is intended to be used with the embodiment of the tube (101) illustrated on FIG. 9. FIG. 9 is a diagram of the upper end of the tube (101) of FIG. 5, facing the end on which the filter membrane (102) is fixed. FIG. 9 shows the upper end of the tube (101) which includes:
  the annular shoulder (115),
  the tapered section S2 which inner surface to the tube (101) is clearly visible on FIG. 9, and which outer surface is almost totally hidden on the figure, due to the view in perspective,
  the inner face of the junction between the tapered section S2 and the cylindrical section S1 of the tube (101), which junction is materialized, in this embodiment, by the presence of an annular shoulder (116) comprising a series of protruding elements or pins (117).

In some embodiments of the device, not shown on the figures, a series of protruding elements or pins, of the type of those illustrated on FIG. 9, is arranged in the central part of the section 51 of the tube (101). This specific series of protruding elements or pins may aim at stopping the piston (104) in an intermediate height position, which makes possible to stop the volume expansion of the block of absorbent material at the desired height, and therefore at a desired volume level, in the tube (101). Stopping the volume expansion of the block of absorbent material causes the sample liquid flow towards the device of the invention to be discontinued and thus stops the adsorption of additional bioparticles on the surface of the filter membrane. These particular embodiments of the device of the invention make it possible to control the number of bioparticles adsorbed on the surface of the filter membrane, and thus also to control the density of bioparticles adsorbed on the surface of the filter membrane, at the end of the bioparticle collecting step. It goes without saying that controlling the number of bioparticles collected from the sample, including controlling the density of the particles adsorbed on the filter membrane, contributes to further improve the quality of the specimen to be analyzed.

In the embodiment of the device of the invention which is illustrated on FIGS. 8 and 9, the piston (104) is inserted into the inside of the tube (101), if applicable by applying an angle between the axis of the rod (107) and the vertical axis of the tube (101), so as to engage the pusher means (108) without difficulty. Then, after having engaged the pusher means (108) into the inside of the tube (101), a vertical movement is exerted to the piston (104), parallel to the vertical axis of the tube (101) and (i) the one or more slot(s) (112) of the disk (110) of the piston (104) is or are shifted to coincide with the one or more corresponding protruding elements (117) of the tube (101). Then the translational motion is continued until the piston (104) is totally engaged in the tube (101), that is to say until the lower surface of the pusher means (108) be in contact with the block (103) of absorbent material. This embodiment which includes the combination of (i) a piston (104) comprising a disk (110) provided with one or more slots (112) and (ii) a tube (101) comprising a shoulder (116) provided with one or more corresponding protruding elements (117), enables an easy engagement of the piston (104) into the inside of the tube (101), and simultaneously prevents any unwanted disengagement of said piston (104). With this particular embodiment of the device, the probability is low that once the piston (104) is engaged into the inside of the tube (101), the one or more slots (112) and the one or more corresponding protruding elements (117) coincide again, which would cause the disengagement of said piston.

In these embodiments previously described, wherein the device of the invention is provided with a series of protruding elements or pins on the central part of the Section S1 of the tube (101), the vertical movement of the piston (104) resulting from the volume expansion of the block of absorbent material is stopped because of the piston disk (110) contacting said protruding elements or pins.

In yet other embodiments of the device of the invention, the pusher means (108) also comprises one or more slots (112), generally which size and position are the same as those of the slots (112) present on the disk (110). In some preferred embodiments, the one or more slot(s) (112) of the disk (110) and the one or more slot(s) of the pusher means (108) are each vertically aligned to one another, along the main axis of the rod (107). In other preferred embodiments, the one or more slot(s) of the pusher means (108) are offset from each other, along the main axis of the rod (107), which further reduces the risk of disengagement of the piston (104). In every instance, in these other embodiments of the device, the engagement of the piston (104) into the inside of the tube (101) is easy, without increasing the risk of disengagement of said piston.

It is also an object of the present invention to provide a method for capturing suspended bioparticles in a liquid medium, including the following steps of:
a) placing a bioparticle capture device such as described hereabove in a container containing a liquid medium with bioparticles suspended therein,
b) maintaining the device in said container for a time sufficient for capturing at least part of the bioparticles contained in the liquid medium on the outer surface of the filter membrane (102) of the device (101).

The device of the invention such as configured at the beginning of step a) of the hereabove method is illustrated respectively on each of FIGS. 1 and 5.

Advantageously, the container containing the bioparticle suspension is of a known type, for example a flask traditionally used for conditioning cell or tissue samples for biological analyses, including cytological and histological analyses.

Further, the liquid medium containing the suspended biological particles is of a known type. Most of the time, when the planed cytological analysis consists in an analysis of cell types on micro slides, said liquid consists in an aqueous buffered liquid containing a substance for fixing suspended cells or cell bodies. To be especially mentioned as a fixation agent are alcohol based mixtures. For example, one may use the alcohol based fixation agent marketed under the trade name SEDFIX® by the SURGIPATH society or the one marketed under the trade name PRESERVCYT® by the Cytyc society or the one marketed under the trade name EASY-FIX® by the Labonord society. In other embodiments, for example when a later cytological analysis is performed from living cells, said liquid may consist in a saline buffer medium, preferably in a suitable cell culture medium. In yet other embodiments, said liquid may consist in a natural body fluid such as urine, or in a pathologically secreted body fluid, like an ascite, an effusion, a cyst or a flow.

The time duration of step a) is variable. It corresponds to the time required for the device of the invention to move from its store position to the position contacting the bioparticle suspension to be treated.

In step b), generally the end of the tube (101) provided with the filter membrane (102) only needs to be in contact with the liquid medium and the totality of the outer surface of the filter membrane be immersed in said liquid medium. A liquid medium flow is then generated through the filter membrane (102) to the inside of the tube (101), and more particularly towards the block (103) of absorbent material which is positioned at this end of the tube (101). The incoming liquid medium flow is generated both (i) through the surface tension force resulting from the surface energy characteristics of the block (103) of absorbent material and (ii) through the suction mechanical action of the liquid medium resulting from the gradual increase in volume of the absorbent material that constitutes the block (103).

In step b) the incoming liquid medium flow carries bioparticles away to the inside of the tube (101), the particles being, depending on the nature of the initial biological sample and on the pore size of the filter membrane (102), for all or for part only retained on the outer surface of the filter membrane (102) in contact with the liquid medium.

The time duration of step b) may be easily adapted by the person skilled in the art, by taking all the various criteria into account, such as (i) the expected final density of the bioparticles retained on the filter membrane, (ii) the concentration of suspended bioparticles in the initial liquid medium and (iii) the absorption capacity of the block (103) of absorbent material.

Generally speaking, whatever the embodiment of the device of the invention which is used, the time duration of step a) is of at least 5 seconds, a time required for generating the incoming liquid flow towards the inner volume of the tube (101) causing the capture of a minimal number of sufficient bioparticles on the surface of the filter membrane (102).

It has been shown according to the invention that with a device such as described hereabove which includes a block (103) of absorbent material in compressed viscose, the capture on the filter membrane (102) of a bioparticle number adapted to their subsequent cytological analysis is obtained for a time duration of step b) ranging from 5 seconds to several minutes, depending on the nature of the initial biological sample, and in particular on the concentration of suspended bioparticles in the initial liquid medium. The time duration of step b) may be conditioned by the clogging of the filter membrane pores by the particles, which causes the absorption to be almost completely stopped and the particles to come as thin layers, without requiring any sophisticated measuring device.

Figure 2:
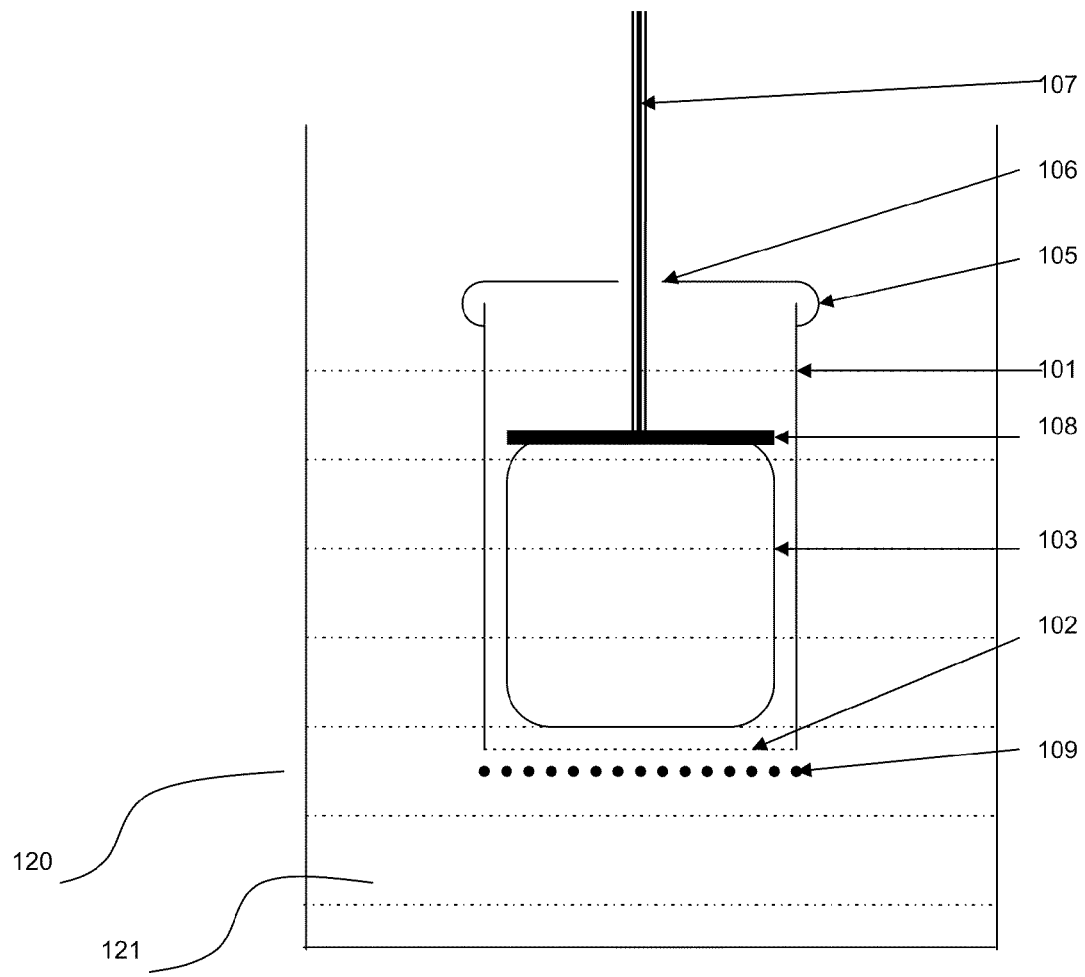
FIG. 2 is a diagram illustrating a vertical cross-section along the symmetry axis of one embodiment of the bioparticle capture device, when the device has been dipped, without being totally immersed, in a container containing the bioparticle suspension to be treated for a time sufficient for retaining the bioparticles on the surface of the filter membrane.
Figure 3:
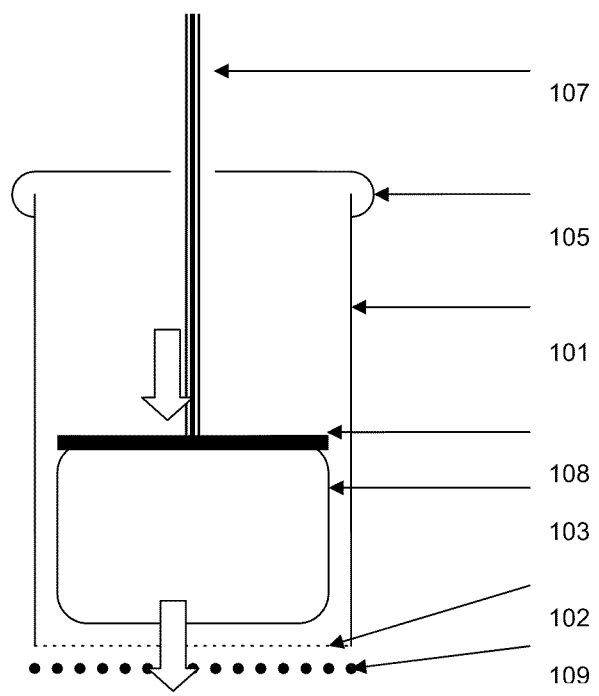
FIG. 3 is a diagram illustrating a vertical cross-section along the symmetry axis of one embodiment of the bioparticle capture device, after retention of the bioparticles on the filter membrane, when the piston rod is actuated for exerting a pressure on the absorbent block, so as to generate a liquid flow to the outside of the device aiming at removing the bioparticles from the filter membrane. On FIG. 3, the arrows represent the direction to which the piston is actuated.

At the end of step b), the position of the device is as illustrated on the drawing of each of FIGS. 2 and 6. On each of FIGS. 2 and 6, the device of the invention is presented immersed in the container containing the suspended bioparticles in a liquid medium. The block (103) of absorbent material increased in volume, with respect to its dry state initial volume illustrated on each of FIGS. 1 and 5. The bioparticles (109), initially suspended in the liquid medium and thereafter retained, are illustrated on the outer surface of the filter membrane (102) on FIG. 2. On each of FIGS. 2 and 6, the piston (104), which bearing means (108) still contacts the upper surface of the block (103) of absorbent material, moved to its upper position as a consequence of the absorbent material swelling.

At the end of step b) of the method, the bioparticles retained on the outer surface of the filter membrane (102) may be recovered and treated according to traditional methods of cytological analysis, for example transfer through replica plating, by applying a pressure of the piston on the block (103), from the filter membrane (102) towards the surface of a micro slide, then optionally subsequent implementation of a preparation staining step, prior to performing the cytological analysis, such analysis being generally carried out through photon microscopy.

Surprisingly, as illustrated on FIG. 4, it has been shown according to the invention that using the device described in the present description makes it possible to obtain preparations for cytological analysis with a quality at least as good as that of preparations obtained with known systems, including those obtained with the automated systems that were previously described in the present description.

Thus, surprisingly, analyzing a cell preparation obtained by means of the device of the invention shows that the cell integrity is often equally or even better preserved than compared with a preparation made using a known device.

Without wishing to be bound by any theory, the applicant thinks that the best cell integrity which could be observed with the device of the invention is due to the fact that the flow rate of the incoming liquid flow which is generated by the block (103) of absorbent material is reduced as compared to the flow rate of the incoming flow which is generated by known systems, in particular systems wherein said incoming flow is generated by setting under vacuum the compartment placed downstream of the filter membrane. As a consequence, with the device of the invention, the particles stopped by the filter membrane lead to a lower deceleration of the particles and simultaneously to a lower alteration, or even no alteration, of their physical integrity.

The use of the device of the invention has other advantages, in particular when the initial biological sample consists in a sample said to be "hemorrhagic", in which large amounts of fibrinous concretions are present. By using known systems with this type of samples, cytological preparations are typically obtained that are difficult to analyze on micro slides due to the presence of numerous fibrinous concretions that are carried away towards the filter together with the interesting biological particles.

On the contrary, with the device of the invention, superior quality cytological preparations are obtained on micro slides, even where the initial sample consists in a hemorrhagic sample, that is to say the cytological preparations obtained are free or essentially free of fibrinous concretions. The applicant thinks that this additional advantage of the device of the invention is due to the low flow rate of the incoming flow into the device, which does not carry the fibrinous concretions together with the interesting bioparticles.

The use of the device of the invention is also advantageous during a surgery, for example during an ultrasound-guided fine-needle aspiration biopsy in an extemporaneous examination. It will be possible to indicate to the operator if the collected liquid sample is satisfying, making it possible to repeat the procedure if the quality of the collected sample was insufficient. Aspiration biopsies include those for mammary nodules, hepatic metastases or tumors in deep organs. Such a use of the device of the invention enables to reduce the risk of repeated surgical procedures, which invasive aspect causes unnecessary traumatisms in patients.

As has already been mentioned hereabove, the device of the invention is used in methods for making cytological preparations.

Thus, the present invention also relates to a method for making a cytological preparation from a liquid medium containing suspended bioparticles, comprising the following steps of:
  a) placing a device such as defined in the present description in a container containing a liquid medium with biological particles suspended therein,
  b) maintaining the device in said container for a time sufficient for capturing at least part of the biological particles contained in the liquid medium on the outer surface of the filter membrane (102) of the device,
  c) removing the device from said container, if applicable by pulling on the rod (107) of the piston (104), and
  d) recovering at least part of the biological particles retained on the filter membrane of the device.

In advantageous embodiments of step d) of the hereabove method for making cytological preparations, a pressure is exerted onto the block (103) by actuating the piston (104), so as to generate a liquid flow coming out from the inside of the device (101) to the outside, said liquid flow causing the bioparticles initially retained on the filter membrane to be carried away. This particular embodiment of the method is illustrated on each of FIGS. 3 and 7.

Once removed from the filter membrane (102), the interesting bioparticles are recovered and thereafter submitted to one or more steps so as to be pre-treated before their cytological analysis.

Generally, the particles retained on the filter membrane (102) of the device of the invention, in step d), are recovered according to a method traditionally used by the anatomical pathologists, such as a transfer through replica plating from the filter membrane to the surface support of a micro slide, such as the micro slide (200) illustrated on FIG. 7. The biological preparation, generally the cell preparation, which adheres to the surface of the micro slide may then be submitted to one or more steps so as to be pre-treated prior to observation, for example one or more steps of specific or non-specific staining, including staining steps with May-Grünwald Giemsa, the so called "Papanicolaou" staining, staining with alum carmine, eosine, erythrosine, Schorr staining, basic fuschin, Mayer's hemalum, haematein, haematoxylin, Sudan black, mucicarmin, nigrosin, orcein, phloxin b, xylidine Ponceau, Schiff's reagent, Congo red, etc.

As described hereabove, in some embodiments of step d) of the method of the invention for making a cytological preparation, at least part of the bioparticles are transferred from the filter membrane of the device to the surface of a cytological analysis support, by contacting said filter membrane with the surface of said cytological analysis support.

Moreover, in some embodiments, said method comprises the following additional step: e) performing the staining of the biological particles transferred onto the surface of said cytological analysis support.

In yet other embodiments of step d) of the method of the invention for making a cytological preparation, at least part of the bioparticles are transferred from the filter membrane of the device to a suitable container, for example a cell culture tube, so as to obtain a cytological preparation in the form of a cell concentrated suspension.

The cell concentrated suspension obtained at the end of step d) may then be submitted to one or more subsequent treatment steps, prior to the cytological analysis.

Illustratively, the cell concentrated suspension obtained at the end of step d) may be incubated in the presence of detectable antibodies, specific to membrane markers or to intracellular markers, prior to the cytological analysis which may be carried out for example using a flow cytometry method, if applicable after an additional incubation with the labeled antibodies.

Further, the cell concentrated suspension obtained at the end of step d) may then be treated using molecular biology methods, for example through in situ hybridization using specific nucleic probes or through RNA extraction, then quantization of the expression level of one or more interesting genes, or through DNA extraction, then detection of the mutations within the sequence of one or more interesting genes.

In further embodiments of step d) of the method of the invention for making a cytological preparation, at least part of the bioparticles retained on the filter membrane are recovered by scraping said filter membrane.

In some embodiments, it is possible to separate the filter membrane (102) from the rest of the device, and to perform the embedding of the whole filter membrane/bioparticles retained in the paraffin.

Scraping the filter membrane may be effected by any suitable device of a known type. As an illustration, one may use spatulas traditionally used in cell culture for suspending cultured cells which adhere to the culture support, these spatulas being also called "cell scrapers".

These latter embodiments of the method of the invention are advantageously implemented when tissue micro-fragments have to be recovered so as to be analyzed. As an illustration, micro-fragments thus recovered may then be embedded in paraffin, or in any other type of suitable resin, for making histological sections which will be studied through microscopy techniques, if applicable after having been submitted to one or more suitable histochemical staining or immunohistochemical staining steps. These embodiments of the method of the invention are very especially implemented for performing cytological analyses of bioparticles collected from mucous tissue by scraping.

Most particularly, the device of the invention enables to recover tissue and cell micro-fragments to be later histologically analyzed. This aspect of the device is particularly useful, in view of the increasing development of sampling techniques by needle biopsy or scraping or cytological brushing of tissues, with methods using automated guiding procedures in endoscopies assisted with medical imaging systems. Indeed, this kind of sampling which is nowadays more and more practiced enables to collect sample materials said to be "mixed", also called "cyto-biopsical" materials. There are composite biological materials comprising both full size cells and tissue micro-fragments.

Aiming at further optimizing the implementation of cytological analysis procedures with a bioparticle capture device such as defined in the present description, a multi-assay platform was developed, comprising a plurality of devices of the invention, said multi-assay platform having been conceived for simultaneously making a plurality of cytological preparations from initial biological samples.

Figure 10:
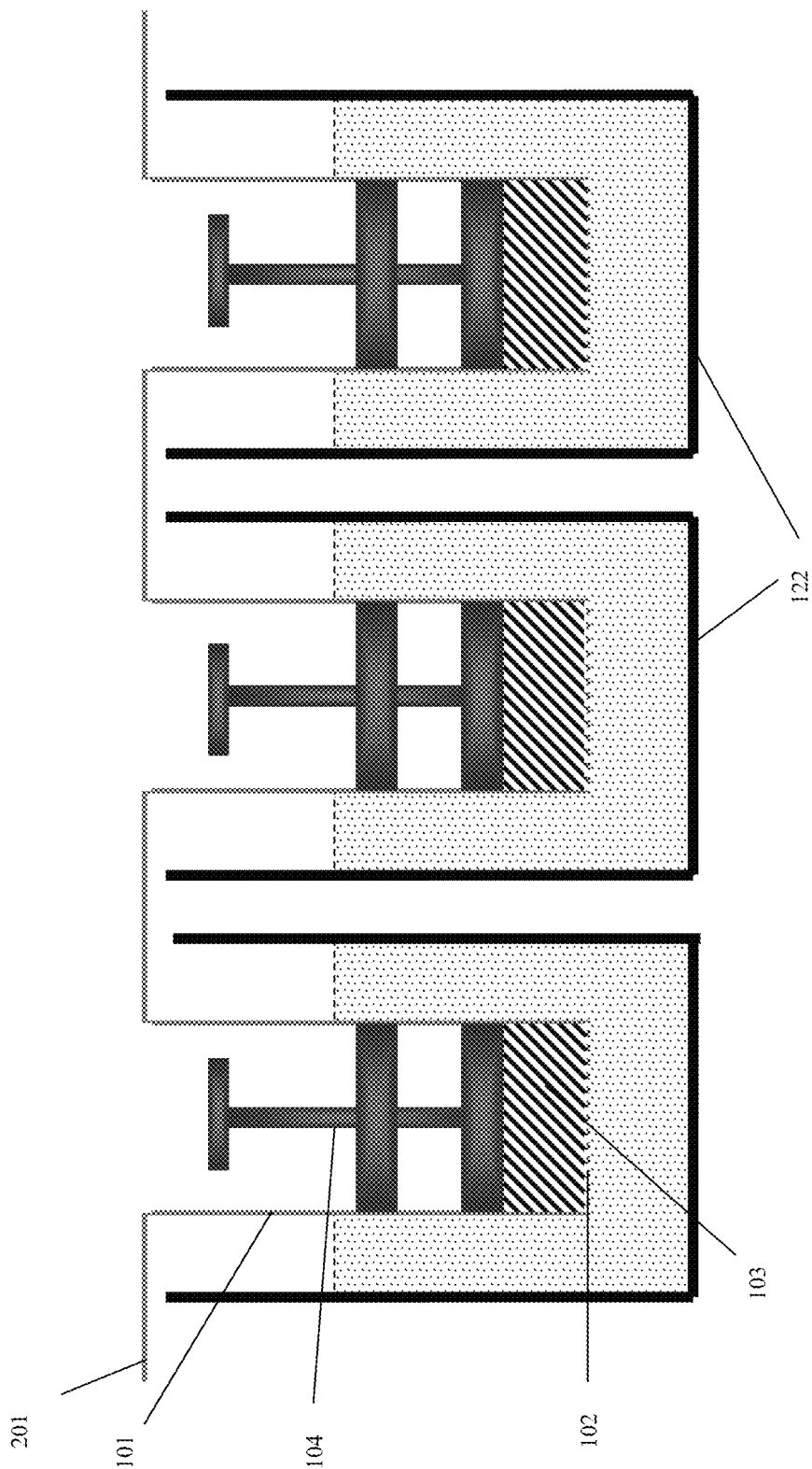
FIG. 10 is a diagram illustrating a partial view of a multi-assay platform in vertical cross-section along the symmetry axis, immediately after having dipped the devices included in said platform into a plurality of containers containing a biological fluid to be analyzed.

Referring to FIG. 10, which is a vertical cross-section of a partial view of a multi-assay platform of the invention, said platform comprises a plurality of bioparticle capture devices which are arranged in a determined manner on the surface of said platform. FIG. 10 shows a series of three aligned devices of the invention in the multi-assay platform.

In some embodiments of a multi-assay platform of the invention, said multi-assay platform comprises a plurality of bioparticle capture devices which are aligned. In these embodiments, the multi-assay platform advantageously comprises a number of bioparticle capture devices of at least 2 and of not more than 100.

"Of at least 2" is intended to include at least 3, 4, 5, 6, 7, 8, 9, 10, 11, 12, 13, 14, 15, 16, 17, 18, 19, or 20. "Of not more than 100" is intended to include at most 99, 98, 97, 96, 95, 94, 93, 92, 91, 90, 85, 80, 75, 70, 65, 60, 55, 50, 45, 40, 35, 30, 25, 24, 23, 22, 21 or 20. In these embodiments of the multi-assay platform, said platform comes in the form of an array comprising a plurality of bioparticle capture devices arranged to each other along a single linear axis.

In some other embodiments of multi-assay platform, the plurality of bioparticle capture devices are arranged both along a plurality of lines that are parallel to each other and along a plurality of columns that are parallel to each other and perpendicular to the lines. Each line and each column comprises a plurality of bioparticle capture devices. When the number of devices of the invention in each line is the same as the number of devices in each column, the multi-assay platform may have a square form. In these embodiments of the multi-assay platform, each line or each column advantageously comprises a number of bioparticle capture devices of minimum 2 and of maximum 100.

As can be easily understood, any other type of mutual arrangements of the bioparticle capture devices within a multi-assay platform of the invention is incorporated in the present invention.

In the embodiment of a multi-assay platform illustrated on FIG. 10, the bioparticle capture devices are all included in a structure of the monoblock type. In this embodiment, the wall of a first tube (101) and the wall of a second tube (101) near to the first tube are connected to each other through the upper surface of the platform. In this embodiment, (a) the wall of a first tube (101), (b) the wall of a second tube (101) near to the first tube and (b) the surface of the platform connecting both walls to each other, form a continuous outer surface, which materializes the structure of the monoblock type of said platform. In this embodiment coming as a monoblock, the structure of the multi-assay platform including the walls of each of the tubes (101) included therein, may be made by simply molding a polymer material such as polyethylene, polystyrene or polypropylene, using methods that are well known from the person skilled in the art. A filter membrane (102) is then mounted, supported by both tubes (101). Thereafter each of the tubes (101) is then fitted with a block (103) of absorbent material, prior to positioning a piston (104).

In other embodiments of the multi-assay platform of the invention, the structure of the platform comes in the form of a plate in which a plurality of recesses have been arranged in a well-ordered manner, each recess being intended to receive a bioparticle capture device, according to its general embodiment described in details hereabove in the present description. The number and the space arrangement of the recesses in the multi-assay platform structure includes the possibilities described previously for the space arrangement of tubes (101) included in the platform of the monoblock type.

As is shown on FIG. 10, each bioparticle capture device included in the multi-assay platform is intended to be introduced into a container containing a biological sample to be tested. In practice, the arrangement of the containers should be compatible with the arrangement of the devices included in the multi-assay platform. To satisfy such technical constraint, the containers containing the biological samples to be tested are advantageously installed beforehand in a sample rack, making it possible to arrange said containers in a compatible position with respect to the devices within the multi-assay platform.

The positioning of the tubes as sampling containers in the sample rack is "compatible" with the arrangement of the devices included in the multi-assay platform when each of said devices contained in the platform can be introduced into each of the containers arranged in said sample rack. Of course the multi-assay platform may comprise a higher number of bioparticle capture devices as compared to the number of containers actually arranged in the sample rack. In such a situation, a cytological analysis of all the samples contained in said containers may be performed, even if all the devices contained in the multi-assay platform are not used.

Most preferably, there are as much bioparticle capture devices in the multi-assay platform as containers in the corresponding sample rack.

Moreover, the multi-assay platform of the invention can be used in the same way as a bioparticle capture device, which has already been detailed hereabove in the present description.

Thus, the present invention further relates to a multi-assay platform comprising a plurality of bioparticle capture devices such as defined in the present description.

Preferably, said multi-assay platform comes in the form of a monoblock structure.

The present invention further relates to a system for capturing suspended bioparticles in a liquid medium, said system comprising the combination of two elements:
- a first element consisting in a multi-assay platform such as defined hereabove, which includes a plurality of bioparticle capture devices positioned in said platform according to a determined arrangement, and
- a sample rack to receive the biological sample containers, where said containers may be positioned in said sample rack according to an arrangement compatible with the arrangement of the devices in said multi-assay platform.

The present invention also relates to a method for making a cytological preparation from a liquid medium containing suspended bioparticles, comprising the following steps of:
- a) placing at least part of the plurality of bioparticle capture devices (101) contained in a multi-assay platform such as defined hereabove in a container or a plurality of containers, containing each a liquid medium with bioparticles suspended therein,
- b) maintaining the device(s) in said container(s) for a time sufficient for capturing at least part of the bioparticles contained in the liquid medium on the outer surface of the filter membrane (102) of each of the devices (101),
- c) performing a multi-assay platform translation so as to remove the device(s) from said corresponding container(s), and
- d) recovering at least part of the bioparticles retained on the filter membrane of each of the devices contained in the multi-assay platform and having been placed in a container.

Moreover the implementation of the hereabove method is the same as that of the method wherein only one bioparticle capture device is used. Details of such implementation are therefore described hereabove in the present description referring to the method for implementing a single bioparticle capture device.

The invention claimed is:

1. A device for capturing cells suspended in a liquid medium on to a filter membrane, for preparing samples for cytological analysis, the device comprising:
   a tube comprising first and second ends,
   the first end of said tube being closed by the surface of a filter membrane adhered to or welded to the thickness of the walls of said tube,
   a piston comprising a rod connected to a bearing at one end of the rod, said piston configured to fit inside the tube and to freely slide in the tube along an axis parallel to the walls of the tube, and
   a block of hydrophilic absorbent material placed inside the tube, the absorbent material positioned adjacent to the inner surface of the filter membrane and between the inner surface of the filter membrane and the piston bearing,
   wherein the bearing has a shape that matches the shape of the inner diameter of the tube, but has a size that is smaller than the inner diameter of the tube so that the edges of the bearing are not continuously contacting the surface of the inner wall of the tube and so that the piston can freely slide when inside the tube, and
   wherein the absorbent material can absorb the liquid medium, with the medium passing through the filter membrane and into the absorbent material while the cells are trapped on the outer surface of the filter membrane.

2. The device according to claim 1, wherein the hydrophilic absorbent material swells when contacting the aqueous liquid medium.

3. The device according to claim 1, wherein the hydrophilic absorbent material comprises compressed viscose.

4. The device according to claim 1, wherein the filter membrane has a pore size in a range from 1 μm to 25 μm.

5. The device according to claim 1, wherein the second end of said tube is covered by a plug comprising a central hole through which the piston rod protrudes.

6. The device according to claim 1, wherein a disk is fixed on the rod, the diameter of said disk being determined so as to allow the sliding of the rod along an axis parallel to the walls of the tube.

7. The device according to claim 1, wherein said tube comprises two sections forming a continuous outer surface, respectively:
   a first section S1 of the cylindrical type, one end of which is the first end of said tube which is closed by the surface of a filter membrane, and the other end forms a continuous outer surface with a third section, and
   the third section S2 having a tapered shape, an end with the smallest diameter forming a continuous outer surface with said first cylindrical section, and an end with the largest diameter is a second end of the tube.

8. The device according to claim 7, wherein the end with the largest diameter of the section S2 of the tube comprises a flat, annular shoulder perpendicularly to the edges of the section S1 of the tube.

9. The device according to claim 1, wherein the absorbent material can swell to at least a two-fold increase in volume through the absorption of the liquid medium, compared to its initial dry volume.

10. The device according to claim 1, wherein the absorbent material can swell to at least a four-fold increase in volume through absorption of the liquid medium, compared to its initial dry volume.

11. The device according to claim 1, wherein the filter membrane has a pore size in a range from 5 μm to 10 μm.

12. A method for capturing suspended cells in a liquid medium, comprising:
   a) placing the device according to claim 1 in a container containing the liquid medium with the cells suspended therein, and
   b) absorbing the liquid medium through the filter membrane and into the absorbent material, while trapping the cells on the outer surface of the filter membrane.

13. A method for making a cytological preparation of cells, comprising:
   a) placing the device according to claim 1 in a container containing the liquid medium with the cells suspended therein,
   b) absorbing the liquid medium through the filter membrane and into the absorbent material, while trapping the cells on the outer surface of the filter membrane,
   c) removing the device from said container, and
   d) recovering the cells trapped on the filter membrane.

14. The method according to claim 13, wherein in step d), a pressure is exerted onto the block of hydrophilic material by actuating the piston, so as to generate a liquid flow from the inside of the device to the outside, said liquid flow causing detachment of the cells retained on the filter membrane.

15. The method according to claim 13, wherein in step d), the cells are transferred from the filter membrane of the device onto a surface of a cytological analysis support, by contacting said filter membrane with the surface of said cytological analysis support.

16. The method according to claim 15, further comprising:
e) staining the cells transferred onto the surface of said cytological analysis support.

17. The method according to claim 13, wherein in step d), the cells are transferred from the filter membrane of the device to a container, for obtaining a cytological preparation in the form of a cell suspension.

18. The method according to claim 13, wherein in step d), the cells trapped on the filter membrane are recovered by scraping said filter membrane.

19. A multi-assay platform comprising a plurality of devices according to claim 1.

20. A system for capturing cells suspended in a liquid medium, said system comprising:
the multi-assay platform according to claim 19, the plurality of devices being positioned in said multi-assay platform according to a determined arrangement, and
a sample rack to receive a plurality of biological sample containers, wherein said containers are positioned in said sample rack according to an arrangement that is compatible with the arrangement of the devices positioned in said multi-assay platform.

* * * * *